(12) United States Patent
Gurvich et al.

(10) Patent No.: US 9,403,037 B2
(45) Date of Patent: Aug. 2, 2016

(54) METHOD OF DOSE COMPARISON FOR IN VIVO DOSIMETRY

(71) Applicants: Victor Alexander Gurvich, Alexandria, VA (US); John Marian Pacyniak, Lorton, VA (US)

(72) Inventors: Victor Alexander Gurvich, Alexandria, VA (US); John Marian Pacyniak, Lorton, VA (US)

( * ) Notice: Subject to any disclaimer, the term of this patent is extended or adjusted under 35 U.S.C. 154(b) by 305 days.

(21) Appl. No.: 14/050,337

(22) Filed: Oct. 10, 2013

(65) Prior Publication Data

US 2014/0107392 A1  Apr. 17, 2014

Related U.S. Application Data

(60) Provisional application No. 61/714,228, filed on Oct. 16, 2012.

(51) Int. Cl.
*A61N 5/10* (2006.01)

(52) U.S. Cl.
CPC ............ *A61N 5/1075* (2013.01); *A61N 5/1071* (2013.01)

(58) Field of Classification Search
CPC .......................... A61N 5/1071; A61N 5/1075
See application file for complete search history.

(56) References Cited

U.S. PATENT DOCUMENTS

2011/0135058 A1* 6/2011 Sgouros et al. ................. 378/65
2014/0105355 A1* 4/2014 Toimela et al. ................. 378/41

OTHER PUBLICATIONS

Gurvich et al. "Useful Techniques for Tomotherapy Treatment Planning", IFMBE Proceedings 25/I, pp. 890-892, 2009.*
Wachter-Gerstner et al. "Bladder and rectum dose defined from MRI based treatment planning for cervix cancer brachytherapy: comparison of dose-volume histograms for organ contours and organ wall, comparison with ICRU rectum and bladder reference point" Radiotherapy and Oncology 68 (2003) pp. 269-276.*

* cited by examiner

*Primary Examiner* — Christine H Matthews
*Assistant Examiner* — Kaylee Wilson

(57) ABSTRACT

The invention relates to in vivo dosimetry techniques and can be used for comparison of dose measured in reference point and dose calculated at the same place with computerized treatment planning system. The suggested method takes into consideration dose difference and distance-to-agreement between measured and calculated points and uses a region of measurements (ROM) contoured as an organ at risk so that dose differences inside the ROM and acceptance interval are defined with the dose volume histogram of the ROM. The method can be used for evaluation of influence of ROM homogeneity and dosimeter movement on the difference between calculated and measured doses.

9 Claims, 3 Drawing Sheets

METHOD OF DOSE COMPARISON FOR IN VIVO DOSIMETRY

We claim priority of provisional application No. 61/714,228 of Oct. 16, 2012

BACKGROUND OF THE INVENTION

The invention relates to in vivo dosimetry techniques that are used to record the dose received by patient during radiation therapy treatment and for detection of errors during treatment delivery. It can be applied for comparison of the dose measured in reference point and dose calculated at the same place with computerized treatment planning system (TPS) such as Pinnacle or Eclipse.

The measurement of a total dose that a patient receives during a radiotherapy process is usually implemented with a small dosimeter like diode, TLD or OSLD (nanodot) which is placed on a patient's skin at the location prescribed by a physician or selected by a dosimetrist. The dosimeter is often covered by bolus, a tissue equivalent material with about 0.5 cm thickness or more depending on the energy of applied radiation (report of TG 62 of the Radiation Therapy Committee "Diode in vivo dosimetry for patients receiving external beam radiation therapy," AAPM report #87, Medical Physics Publishing, Madison, Wis., 2005; International Atomic Energy, "Development of procedures for in vivo dosimetry in radiotherapy" "IAEA Human Health Report #8, Vienna, Austria, 2013; European Society of Radiation Oncology, "Practical guidelines for implementation of in vivo dosimetry with diodes in external radiotherapy with photon beams (entrance dose)," ESTRO Booklet #5, Brussels, Belgium, 2001).

A dosimeter can also be placed in a patient hollow organ or be temporary implanted in tissue. Then a patient is irradiated by a beam of X-rays, electrons or other ionizing radiation. After the procedure is finished the dose received by dosimeter is measured with a special device depending on the type of dosimeter. Then the measured dose is compared with the dose at the point of measurements (POM) calculated with TPS.

At present computerized TPS uses points of interest (POI) or reference points to define the dose in the POM. The dose is calculated in the center of the most probable dosimeter location and in several points around it to provide for uncertainties of dosimeter setup and patient's movement. The average dose is defined as the calculated dose in the point of measurement during the radiotherapy procedure. The main shortcoming of this method is that POI are selected arbitrary and a measured dose at the POM can significantly differ from the calculated one (Mijnheer et al. "In vivo dosimetry in external beam radiotherapy," Med. Phys., 40, July 2013). The difference is especially large in brachytherapy dosimetry due to high gradient dose distribution and the large range of dose and dose rate (Tanderum et al. "In vivo dosimetry in Brachytherapy). This discrepancy and impossibility to estimate a confidence interval can cause wrong interpretation of the results of comparison.

Electronic Portal imaging devises are also used for in vivo dosimetry which can provide two- and three-dimensional dosimetric information delivered to patient (W. van Elmpt et al, "3D in vivo dosimetry using megavoltage cone-beam CT and EPID dosimetry," Int. J. Radiat. Oncol., Biol., Phys. 731580-1587, 2009). However, they are oversensitive to photons of low energy, have continued signal after irradiation ceased, and the accuracy of measurements is often not enough because of influence of scattered radiation. Sometimes special devises and software are used for 2D or 3D gamma analysis and DVH comparison during pretreatment IMRT and VMAT verification of dose distribution (Carrasco et al. "3D DVH-based metric analysis versus per-beam planar analysis in IMRT pretreatment verification," Med. Phys. 39, 5040-5049, 2012). However, at this time no pass/fail criteria are available for differences of measured and planned doses. Besides, these techniques use special equipment and sophisticated software, have essentially the same disadvantages as EPIDs, applied for the measurements of dose distribution rather that absolute dose evaluation in the point or region of interest, work with the dose distribution registered for the a certain moment of time and are not practical for routine in vivo dose measurements.

SUMMARY OF INVENTION

The aim of the invention is to improve the accuracy and efficiency of calculation of the dose in the points of measurement and define the limits of dose deviation during in vivo dosimetry.

The method takes into consideration widely used in IMRT QA gamma index where acceptance criteria are dose difference and distance-to-agreement between measured and calculated points. However, instead of gamma index we apply a dose volume histogram (DVH) that can be obtained for any 3D or IMRT plan. For planned dose evaluation in TPS (e.g. Pinnacle) we can use spherical or disk-shaped ROI of certain diameter, e.g. 10 mm contoured as organ at risk or organs included in the organ list instead of POI that are applied in present. This ROI can be called region of measurements (ROM) which is placed in the measurement area and embraces all most probable points of measurements of in vivo dosimeter taking into consideration setup uncertainties and organ movement.

In this case we can analyze DVH and dose distribution in ROM where the dosimeter is placed. For example, if a measured dose is 100 cGy, acceptable DVH dose interval is from D80 to D20, D80 is 60 cGy and D20 is 110 cGy then the measured dose is acceptable.

Differential DVH can also be used for the analysis of acceptable dose interval. For example, the interval can be defined as the full width at half maximum of the DVH, i.e. between minimum and maximum doses at 50% level of the maximum height of DVH graph. It can also be defined as a certain distance from medial dose value.

Two major reasons of discrepancies between planned and measured doses are heterogeneity of irradiated human tissue and a shift of a dosimeter due to setup inaccuracy and patient or organs movement. It is possible to apply the suggested method for quantitative analysis of heterogeneity influence on dose distribution and difference in planned and measured doses. Drawing the region of interest (ROI) around ROM and changing the density of ROI with TPS tools will change DVH of the ROM and the acceptance interval. The heterogeneity factor can be defined as $F_{het}=AI_{hom}/AI_{het}$, where $AI_{hom}$ and $AI_{het}$ are acceptance intervals measured with and without homogenized ROI respectively.

The method can also be used for analysis and verification of setup accuracy and movement of the organ that contain the dosimeter during a treatment. It will be implemented by AI measurements for ROM1 and ROM2 with different length. A moving factor can be defined as $F_{mov}=AI_{mov}/AI_{st}$, where $AI_{mov}$ and $AI_{st}$ are acceptance intervals for ROM1 and ROM2 created for moving and stationary dosimeter.

Dose distribution in ROM can depend on the direction of the moving dosimeter. An anisotropy factor may be defined as $F_{an} = AI_X/AI_Y$, where $AI_X$ and $AI_Y$ are acceptance intervals measured for specially created ROMs oriented in X and Y directions respectively.

Advantages of suggested method:
1. Improved accuracy of calculated dose in the points of measurement.
2. High efficiency of dose calculation and determination of the limits of dose deviation.
3. Rapid and accurate analysis available for dosimetrist, physicist and physician immediately after a treatment plan is created.
4. Solid scientific rationale supported by widely used gamma index criteria in clinical practice.
5. DVH application for the analysis of results.
6. Flexible and justified acceptance criteria.
7. Opportunity to analyze and change dosimeter placement during the treatment planning process.
8. Possibility to analyze influence of ROI heterogeneity, setup inaccuracy and moving of the region of measurements on dose distribution and measurement accuracy.

BRIEF DESCRIPTION OF DRAWINGS

The novel features of the invention are set forth in the appended claims. However, the invented method, its advantages and possible implementations are better understood by reference to the following detailed description and drawings wherein:

DESCRIPTION OF PREFERRED EMBODIMENT

Figure 1:
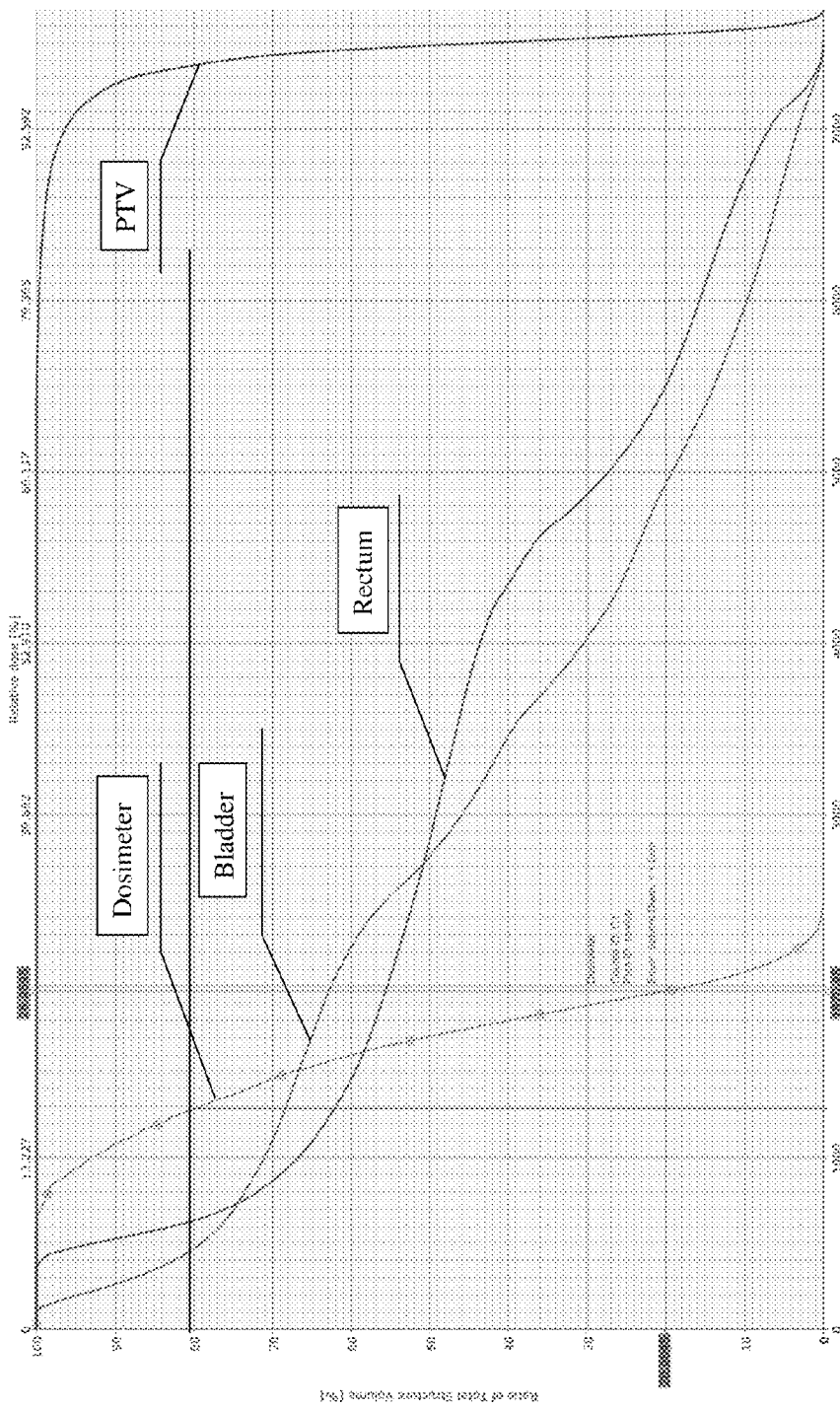
FIG. 1 is a tomographic slice of pelvis. A disc-shaped ROI that is considered as a ROM named "Dosimeter" is located on the top of the surface.

FIG. 1 shows an axial tomographic slice of pelvis. A disc-shaped ROI named Dosimeter is placed on the top of a patient surface. The drawings and dose calculations are implemented with Eclipse TPS. ROM can be created manually or for some TPS placed to the surface from an organ list. In case when dosimeter is placed on the surface of patient body it is convenient to use a transformed eye ball or lens from the organ list of TPS like Pinnacle. The size and shape of the ROM depend on its location, predicted movement of a patient or corresponding organ and expected set up accuracy. IMRT treatment plan with 7 fields is selected for illustration. The suggested method is most effective for IMRT and VMAT or Rapid Arc plans when dose gradient is much higher than in 3D conformal implementation. Brachytherapy and radiosurgery are also areas of prospective applications of the method. Differential DVH of the contoured ROM is shown in the FIG. 1 upper right corner. A vertical line that divides this DVH into two parts corresponds to medial dose that can serve as a center of a selected acceptance interval (AI).

Figure 2:
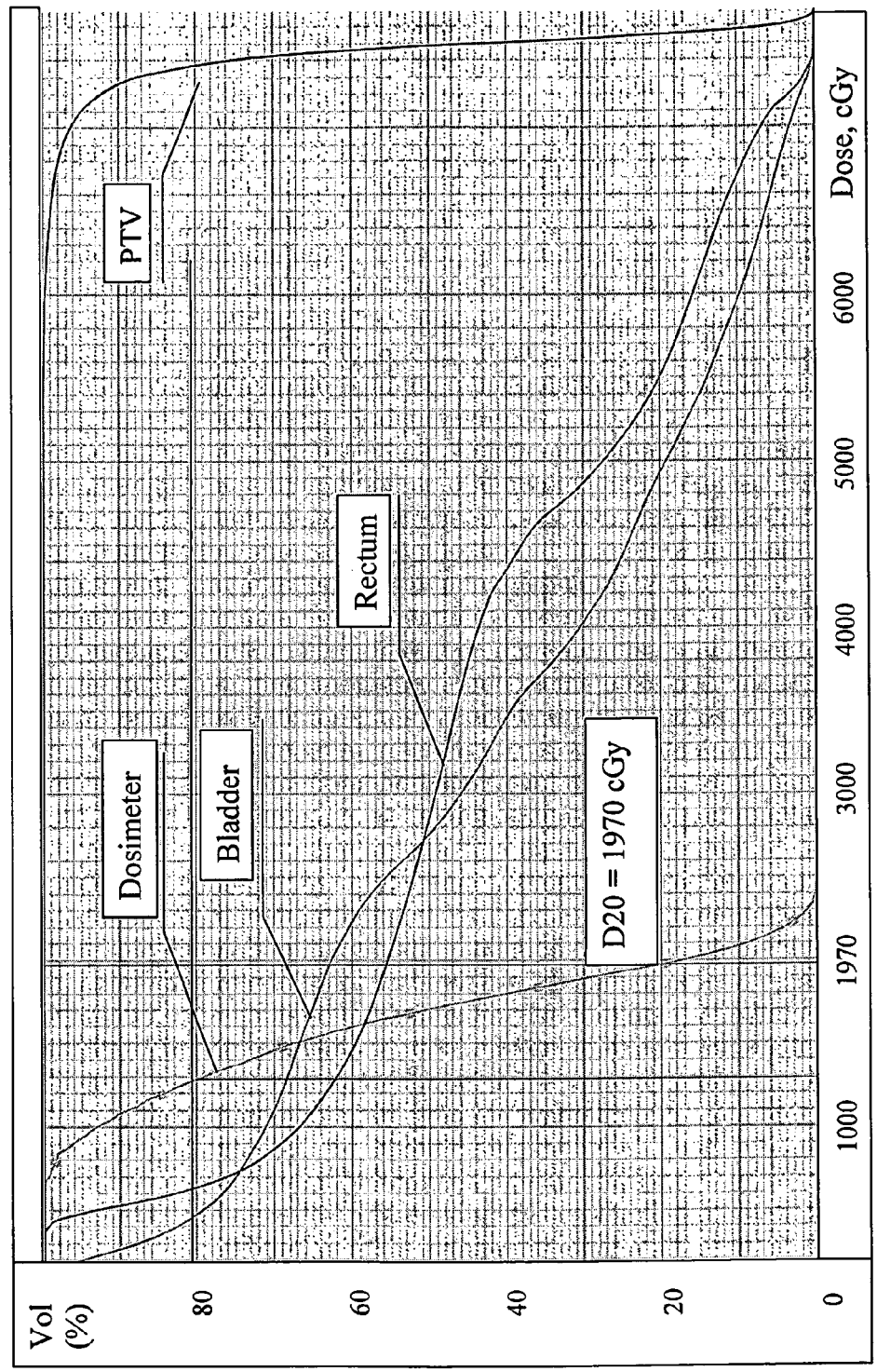
FIG. 2 is a set of cumulative dose volume histograms (DVH) of a target, ROM "Dosimeter" and some organs at risk. The acceptance interval is shown at the dose axis.

FIG. 2 shows the cumulative dose volume histograms (DVH) of the ROM, treatment target (PTV) and organs at risk. It can be seen that the range of doses for different points of ROM is from 700 to 2400 cGy. You can define that the most probable doses measured by dosimeter are confined between D80=1300 cGy and D20=1970 cGy. If ten fractions are used for the entire treatment then for one fraction D80=130 cGy and D20=197 cGy. So, if we consider as a criterion of acceptability the interval between D80 and D20, i.e. acceptance interval, then any measured dose between 130 and 197 cGy is considered acceptable for a patient treatment.

Figure 3:
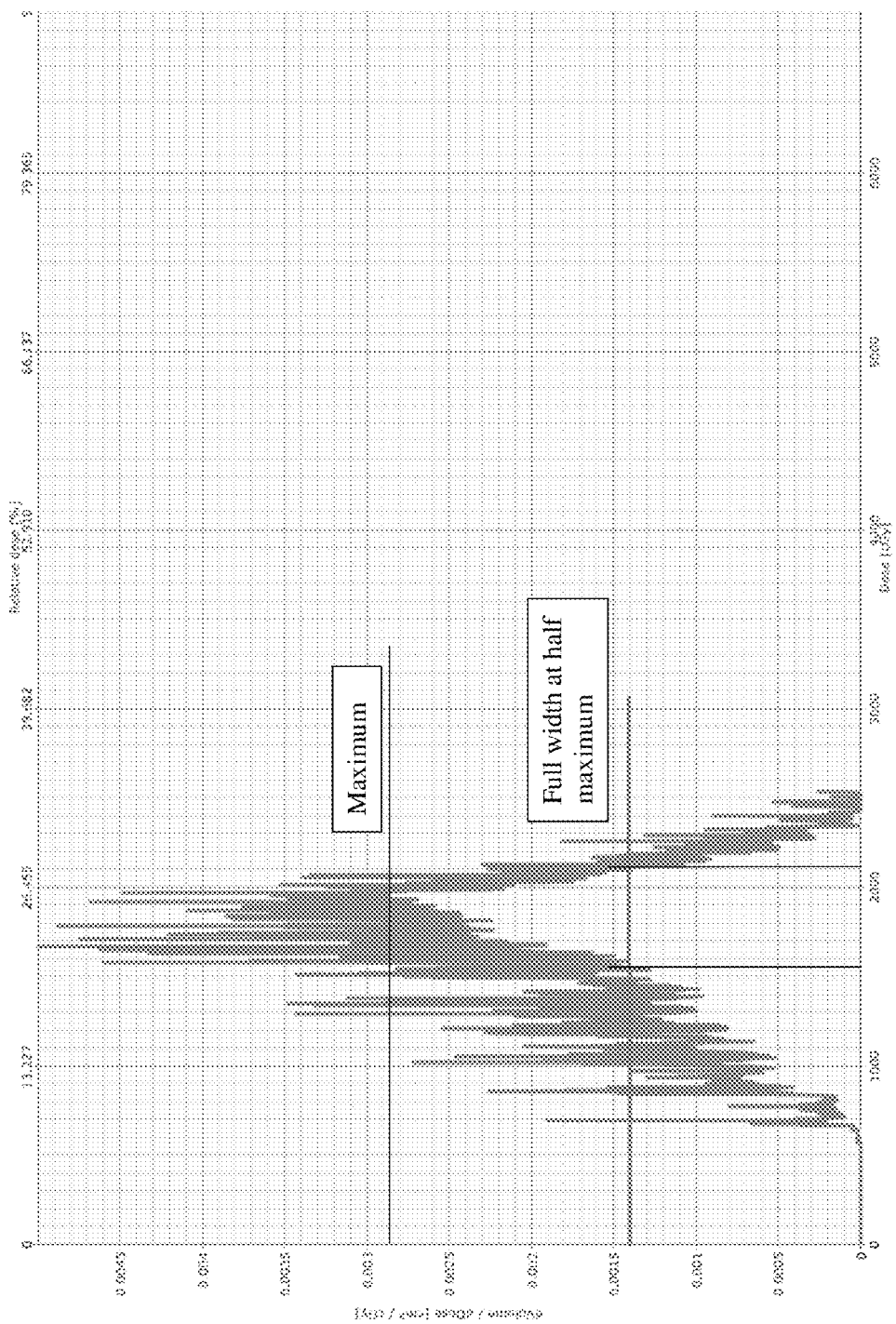
FIG. 3 is a differential DVH of the ROM "Dosimeter." A horizontal line drawn at the half maximum level serves for acceptance interval measuring.

Differential dose volume histogram of the ROM is shown in FIG. 3. Because of the small volume of the ROM its differential DVH is noisy, so the acceptance dose interval can be defined inside the noisy curve. In FIG. 3 the acceptance interval is defined as full width at half maximum of dVolume/dDose [$cm^3$/cGy] value. 50% of dV/dD maximum is 0.0014 (horizontal line in FIG. 3). The acceptance interval (AI) determined with this DVH as its full width at 50% of maximum height is from 1540 cGy to 2100 cGy. As it was mentioned AI can be defined as a certain distance from the medial dose line indicated on differential DVH shown in the upper right corner of FIG. 2.

The difference between doses calculated and measured at the same point is particularly prominent when the selected point is located near the border of tissues with different densities. The heterogeneity causes a high dose gradient in ROM. In order to evaluate the influence of heterogeneity for the results of measurement it is necessary to draw a contour (ROI) around the ROM with margins allowing to get electronic equilibrium in ROM. The size of margin depends on location of the ROM and the energy of ionizing radiation. A heterogeneity factor will be calculated as the ratio of acceptance intervals measured with and without homogenized ROI.

Inaccuracy of dosimeter setup and movement of the point of measurement due to respiration, different fillings of bladder and rectum, losing weight or other factors are major causes of dose deviation for IMRT plans with high gradient of dose distribution in irradiated areas. It is useful to evaluate the influence of dosimeter moving or shift factor on the measured dose. For this purpose it is convenient to represent ROM as a rectangle with a long axis parallel to the direction of movement. The rectangle size or length are depend on the expected intra-fractional of inter-fractional shift. Then a moving or shift factor is defined as the ratio of measured acceptance intervals for ROMs created for moving and stationary dosimeter. Comparing the results of measurement for the ROMs oriented in different directions we can calculate an anisotropy factor as the ratio of acceptance intervals measured for corresponding ROMs.

The invention claimed is:

1. A method of defining acceptable dose limits for an organ at risk during in vivo dosimetry, the method comprising:
   determining a region of measurements (ROM) that defines a volume or area within which a dosimeter is placed during an in vivo dosimetry procedure;
   contouring the ROM as an organ at risk with tools of a treatment planning system;
   creating a treatment plan, calculating and displaying a dose-volume histogram (DVH) of the ROM; and
   using the DV to establish dose differences inside the ROM and an acceptance interval for dose values that can be delivered to any point in the ROM.

2. The method of defining acceptable dose limits for an organ at risk during in vivo dosimetry according to claim 1 wherein the DVH is a differential dose volume histogram of the ROM, and the step of using the DVH to establish dose differences inside the ROM and the acceptance interval for the dose values comprises establishing the acceptance interval using the differential dose volume histogram of the ROM.

3. The method of defining acceptable dose limits for an organ at risk during in vivo dosimetry according to claim 2 wherein establishing the acceptance interval using the differential dose volume histogram of the ROM comprises determining a maximum dVolume/dDose of an area inside a curve of the differential dose volume histogram and defining the acceptance interval as full width at half the maximum dVolume/dDose of the area inside the curve.

4. The method of defining acceptable dose limits for an organ at risk during in vivo dosimetry according to claim 1 wherein the steps of creating a treatment plan, calculating and displaying a DVH of the ROM, and using the DVH to establish the acceptance interval further comprise the steps of drawing a region of interest (ROI) around the ROM, displaying a DVH of an artificially homogenized ROI with the TPS tools, establishing an acceptance interval using the DVH for the artificially homogenized ROI, changing a density of the ROI with the TPS tools, displaying a DVH for the same but non-homogenized ROI, establishing an acceptance interval using the DVH for the non-homogenized ROI.

5. The method of defining acceptable dose limits for an organ at risk during in vivo dosimetry according to claim 4 further comprising a quantitative analysis of heterogeneity influence on dose distribution and differences in planned and measured doses by defining a heterogeneity factor as $F_{het}=AI_{hom}/AI_{het}$, where $AI_{hom}$ and $AI_{het}$ are the acceptance intervals established for artificially homogenized ROI, and for the same but non-homogenized ROI, respectively.

6. The method of defining acceptable dose limits for an organ at risk during in vivo dosimetry according to claim 1 wherein the step of determining a ROM comprises defining a ROM1 for moving dosimeters and defining a ROM2 for stationary dosimeters, wherein ROM1 and ROM 2 have different lengths.

7. The method of defining acceptable dose limits for an organ at risk during in vivo dosimetry according to claim 6 further comprising determining acceptance intervals for ROM1 and ROM2 and performing a quantitative analysis of an influence of setup accuracy and movement of the ROM during a treatment on dose distribution in the ROM by defining a moving factor as $F_{mov}=AI_{mov}/AI_{st}$, where $AI_{mov}$ and $AI_{st}$ are acceptance intervals for ROM1 and ROM2.

8. The method of defining acceptable dose limits for an organ at risk during in vivo dosimetry according to claim 1 wherein the step of determining a ROM comprises defining a specially created ROM1 oriented in an X direction and defining a specially created ROM2 oriented in a Y direction, wherein ROM1 and ROM 2 have different lengths.

9. The method of defining acceptable dose limits for an organ at risk during in vivo dosimetry according to claim 8 further comprising determining acceptance intervals for ROM1 and ROM2 and evaluating an influence of directional dosimeter shift on dose distribution and difference between planned and measured doses by defining an anisotropy factor defined as $F_{an}=AI_x/AI_y$, where $AI_x$ and $AI_y$ are acceptance intervals measured for specially created ROM1 and ROM2 having different lengths with their long axes oriented in X and Y directions, respectively.

\* \* \* \* \*